US009199236B2

(12) United States Patent
Nikonorov et al.

(10) Patent No.: US 9,199,236 B2
(45) Date of Patent: Dec. 1, 2015

(54) BIOLOGIC FLUID SAMPLE ANALYSIS CARTRIDGE WITH SAMPLE COLLECTION PORT

(71) Applicant: Abbott Point of Care, Inc., Princeton, NJ (US)

(72) Inventors: Igor Nikonorov, Whitestone, NY (US); John Blum, Somerset, NJ (US); Douglas R. Olson, Pipersville, PA (US); Marek Turewicz, Lake Forest, IL (US)

(73) Assignee: Abbott Point of Care, Inc., Princeton, NJ (US)

( * ) Notice: Subject to any disclaimer, the term of this patent is extended or adjusted under 35 U.S.C. 154(b) by 55 days.

(21) Appl. No.: 13/731,623

(22) Filed: Dec. 31, 2012

(65) Prior Publication Data

US 2013/0171044 A1 Jul. 4, 2013

Related U.S. Application Data

(60) Provisional application No. 61/582,267, filed on Dec. 31, 2011.

(51) Int. Cl.
*B01L 3/00* (2006.01)
*G01N 35/10* (2006.01)

(52) U.S. Cl.
CPC ............ *B01L 3/508* (2013.01); *B01L 3/50273* (2013.01); *B01L 3/502715* (2013.01); *B01L 3/502738* (2013.01); *G01N 35/1097* (2013.01); *B01L 2200/0605* (2013.01); *B01L 2300/042* (2013.01); *B01L 2300/045* (2013.01); *B01L 2300/049* (2013.01); *B01L 2300/0816* (2013.01); *B01L 2400/0478* (2013.01); *B01L 2400/065* (2013.01)

(58) Field of Classification Search
CPC .................... B01L 3/502715; B01L 3/502738; B01L 2400/065; B01L 2300/045; B01L 2300/087; B01L 2300/0877; B01L 2300/0883; B01L 2400/0622; B01L 2400/0644; B01L 2400/0655; G01N 21/05; G01N 27/44791; G01N 35/1016
USPC .......................................... 436/518; 422/400
See application file for complete search history.

(56) References Cited

U.S. PATENT DOCUMENTS

| | | | | |
|---|---|---|---|---|
| 6,866,823 | B2 | 3/2005 | Wardlaw | |
| 7,850,916 | B2 | 12/2010 | Wardlaw | |
| 2002/0019062 | A1 * | 2/2002 | Lea et al. | 436/518 |
| 2005/0161669 | A1 | 7/2005 | Jovanovich et al. | |

(Continued)

FOREIGN PATENT DOCUMENTS

| | | |
|---|---|---|
| WO | 2005068967 | 7/2005 |
| WO | 2011050110 | 4/2011 |

OTHER PUBLICATIONS

International Search Report for PCT.US2012/072298 dated May 28, 2013.

*Primary Examiner* — Sally Merkling
(74) *Attorney, Agent, or Firm* — O'Shea Getz P.C.

(57) ABSTRACT

A biological fluid sample analysis cartridge is provided that includes a collection port and a body. The body has one or more internal channels in selective fluid communication with the collection port. The collection port includes a collection bowl, and a slide valve assembly operable to be selectively positioned in an open position and a closed position. In the open position, the collection bowl is accessible for sample deposition, and in the closed position the collection bowl is inaccessible for sample deposition.

12 Claims, 5 Drawing Sheets

(56) References Cited

U.S. PATENT DOCUMENTS

2007/0154355 A1 7/2007 Berndt et al.
2011/0117673 A1* 5/2011 Johnson et al. ............... 436/518
2011/0192218 A1 8/2011 Miyamura et al.
2011/0244581 A1 10/2011 Nikonorov
2012/0034647 A1 2/2012 Herzog

* cited by examiner

BIOLOGIC FLUID SAMPLE ANALYSIS CARTRIDGE WITH SAMPLE COLLECTION PORT

The present application is entitled to the benefit of and incorporates by reference essential subject matter disclosed in the U.S. Provisional Patent Application Ser. No. 61/582,267, filed Dec. 31, 2011.

BACKGROUND OF THE INVENTION

1. Technical Field

The present invention relates to apparatus for biologic fluid analyses in general, and to cartridges for acquiring, processing, and containing biologic fluid samples for analysis in particular.

2. Background Information

Historically, biologic fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the cell integrity, accuracy and reliability of the data depends largely on the technician's experience and technique.

In some instances, constituents within a biological fluid sample can be analyzed using impedance or optical flow cytometry. These techniques evaluate a flow of diluted fluid sample by passing the diluted flow through one or more orifices located relative to an impedance measuring device or an optical imaging device. A disadvantage of these techniques is that they require dilution of the sample, and fluid flow handling apparatus.

The collection port through which sample can be collected into the cartridge is an important aspect of the cartridge for purposes of collecting an adequate amount of sample, avoiding spillage, and facilitating safe subsequent handling of the cartridge and the contained sample.

What is needed is an apparatus for evaluating a sample of substantially undiluted biologic fluid, one that can collect a useful amount of sample in a user-friendly manner, one that can securely contain the sample after collection, one that can be readily manufactured, and one that is cost-effective.

DISCLOSURE OF THE INVENTION

According to an aspect of the present invention, a biological fluid sample analysis cartridge is provided that includes a collection port and a body. The body has one or more internal channels in selective fluid communication with the collection port. The collection port includes a collection bowl, and a slide valve assembly operable to be selectively positioned in an open position and a closed position. In the open position, the collection bowl is accessible for sample deposition, and in the closed position the collection bowl is inaccessible for sample deposition.

According to another aspect of the present invention, a biological fluid sample analysis cartridge is provided that includes a collection port and a body. The body has one or more internal channels in selective fluid communication with the collection port. The collection port includes a slide valve assembly operable to be selectively positioned in an open position and a closed position. The slide valve assembly includes a slide body that is received within a channel disposed in the body of the cartridge. The slide body includes a collection bowl, a first passage, and an internal passage having a first end and a second end. In the open position, the collection bowl is accessible for sample deposition, and in the closed position the collection bowl is inaccessible for sample deposition.

The features and advantages of the present invention will become apparent in light of the detailed description of the invention provided below, and as illustrated in the accompanying drawings.

BRIEF DESCRIPTION OF THE DRAWINGS

FIG. 5A shows the slide valve assembly of the collection port in an open position. FIGS. 5B and 5C show the slide valve assembly transitioning between the open position and a closed position. FIG. 5D shows the slide valve assembly of the collection port in a closed position.

FIG. 6A shows the slide valve assembly of the collection port in an open position. FIG. 6B shows the slide valve assembly of the collection port in a closed position.

FIG. 7A is a top planar view that shows the slide valve assembly of the collection port in an open position. FIG. 7B is a top planar view that shows the slide valve assembly in a closed position. FIG. 7C is a partially sectioned end view of the cartridge embodiment shown in FIG. 7B.

DETAILED DESCRIPTION

Figure 1:
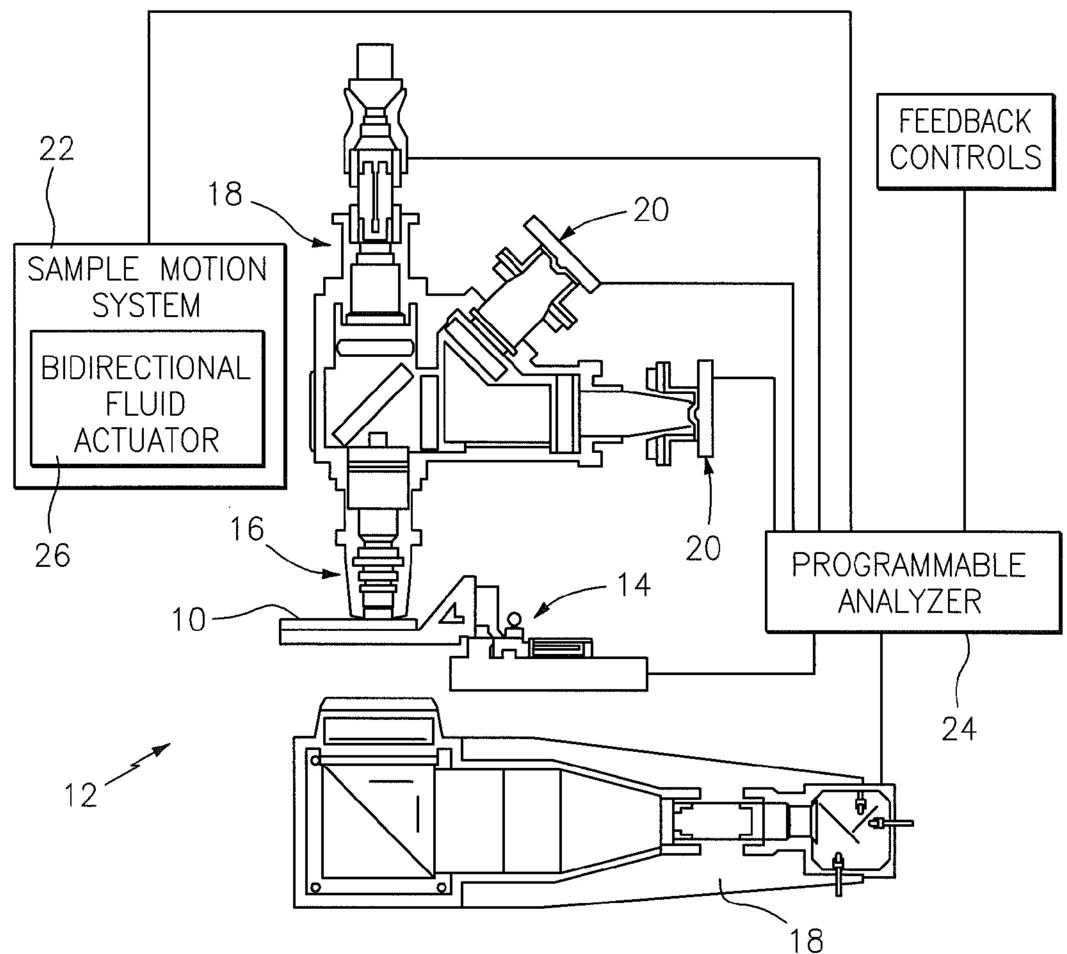
FIG. 1 schematically illustrates an analysis device with which a present invention cartridge may be used.

The present biologic fluid sample cartridge 10 is operable to receive a biologic fluid sample such as a whole blood sample or other biologic fluid specimen, and in some embodiments is also operable to subsequently hold at least a portion of that sample within an analysis chamber. The cartridge 10 can be configured for use in an automated analysis device 12, which device is operable to manipulate and image the sample within the cartridge 10 and subsequently analyze the sample via the image. An example of an analysis device 12 is schematically shown in FIG. 1. The device includes a cartridge positioner 14, a sample objective lens 16, a plurality of sample illuminators 18, at least one image dissector 20, a sample motion system 22, and a programmable analyzer 24. The sample illuminators 18 illuminate the sample using light along predetermined wavelengths. Light transmitted through the sample, or fluoresced from the sample, is captured using the image dissector 20, and a signal representative of the captured light is sent to the programmable analyzer 24, where it is processed into an image for subsequent analysis. The sample motion system 22 permits a fluid motive force (e.g., positive air pressure and/or suction) to access the cartridge 10 to cause the movement of fluid sample within cartridge 10. The sample motion system 22 can include a bidirectional fluid actuator 26 operable to produce fluid motive forces that can move fluid sample within channels disposed in the cartridge 10 in either axial direction. An example of an acceptable bidirectional fluid actuator 26 is a piezo bending disk type pump. The present cartridge 10 is not limited to use with any particular type of fluid actuator, however. The sample motion system 22 can also include a probe operable to selectively engage the cartridge 10 as a means for transferring motive force from the actuator 26 to the cartridge 10. U.S. patent application Ser. No. 13/077,476, which is hereby incorporated by reference in its entirety, discloses an analysis device 12 having a sample motion system 22 with which the present cartridge 10 can be used.

The programmable analyzer 24 includes a central processing unit or other device operable to carry out the instructions of a computer program, to perform the basic arithmetical and/or logical functions, to perform input/output operations of the analyzer 24, etc. (collectively referred to hereinafter as a "CPU"). The CPU is in communication with the cartridge positioner 14, the sample illuminators 18, the image dissector 20, and the sample motion system 22. The CPU is adapted (e.g., programmed) to receive the signals and selectively perform the functions necessary to operate the cartridge positioner 14, the sample illuminators 18, the image dissector 20, and the sample motion system 22

The analysis devices described in U.S. Pat. No. 6,866,823 and U.S. patent application Ser. Nos. 13/077,476 and 13/204,415 (each of which is hereby incorporated by reference in its entirety) are examples of acceptable types of analysis device 12 for use with the present cartridge 10. The present cartridge 10 is not limited to use with these analysis devices, however.

Figure 2:
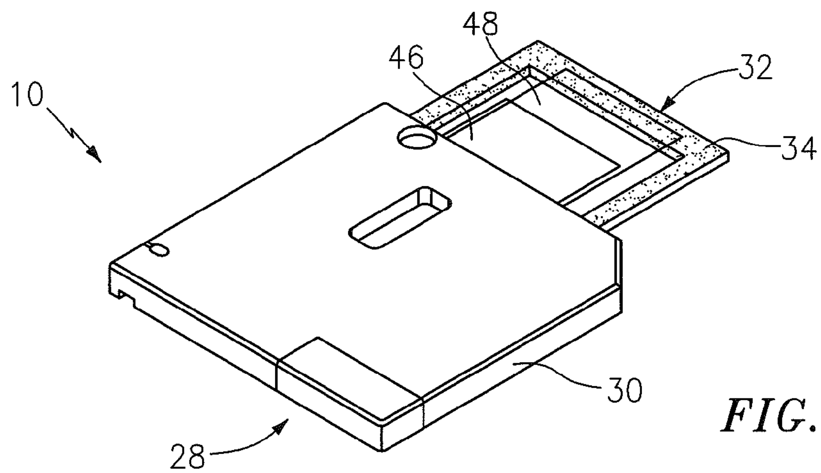
FIG. 2 diagrammatically illustrates a perspective view of an embodiment of the present cartridge, with a slide valve assembly in a closed position and an analysis chamber tray extending outward.
Figure 3:
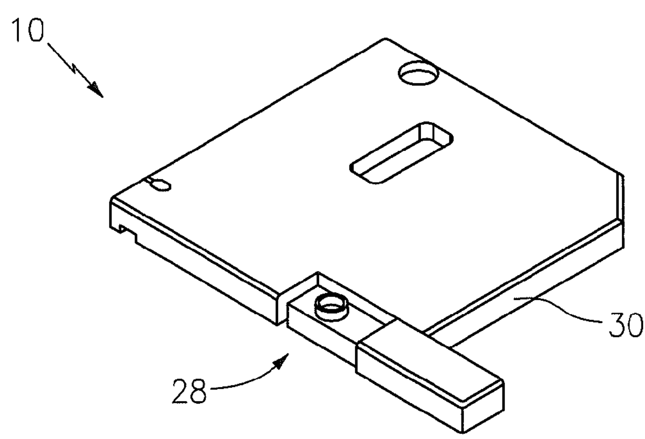
FIG. 3 diagrammatically illustrates the perspective view shown in FIG. 2 with the slide valve assembly in an open position and the analysis chamber tray retracted.

Referring to FIGS. 1-3, the cartridge 10 includes a collection port 28 and a body 30. The collection port 28 is configured to accept a fluid sample from a container (e.g., deposited by needle, etc.), and/or configured to accept a sample from a surface source (e.g., a finger prick). The body 30 is configured to engage and permit sample transfer to an analysis chamber 32. In some embodiments, the analysis chamber 32 is a part of the cartridge 10, and in other embodiments the analysis chamber 32 is separable from the cartridge 10. To facilitate the description of the cartridge 10, the cartridge 10 is described below in an embodiment wherein the analysis chamber 32 is fixed to the cartridge body 30. As stated above, however, the present invention cartridge 10 is not limited to these embodiments and can, for example, be used with a cartridge 10 configured to be used with a separable analysis chamber 32, or a cartridge embodiment wherein the analysis chamber 32 is selectively movable relative to the cartridge body; e.g., an analysis chamber 32 mounted on a tray 34 movable relative to the cartridge body 30 as shown in FIG. 2. U.S. Patent Application Ser. Nos. 61/470,142 and 61/527,114, each of which is hereby incorporated by reference in its entirety, describe cartridge 10 embodiments wherein an analysis chamber 32 is fixed to the cartridge body 30 and one wherein the analysis chamber 32 is mounted on a tray 34, respectively.

Figure 4:
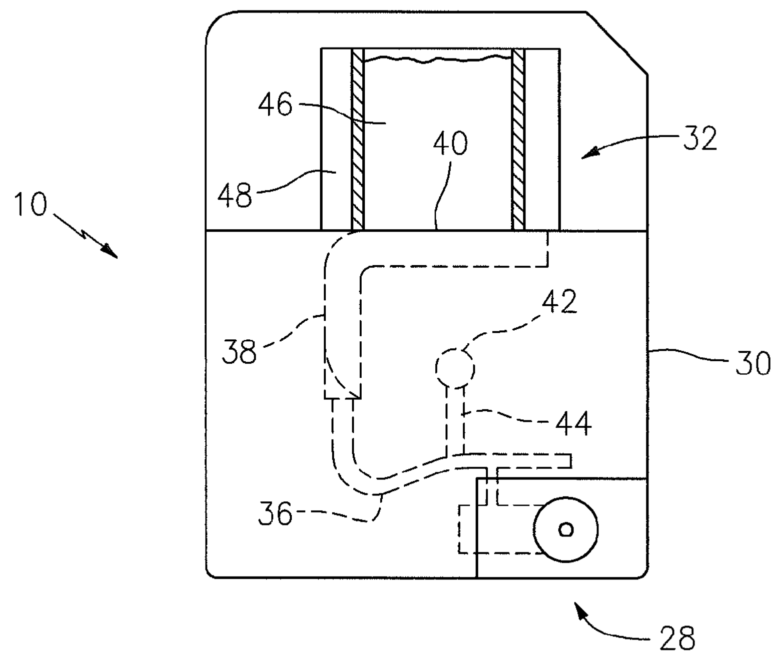
FIG. 4 is a diagrammatic top planar view of a present invention cartridge embodiment.
Figure 5A:
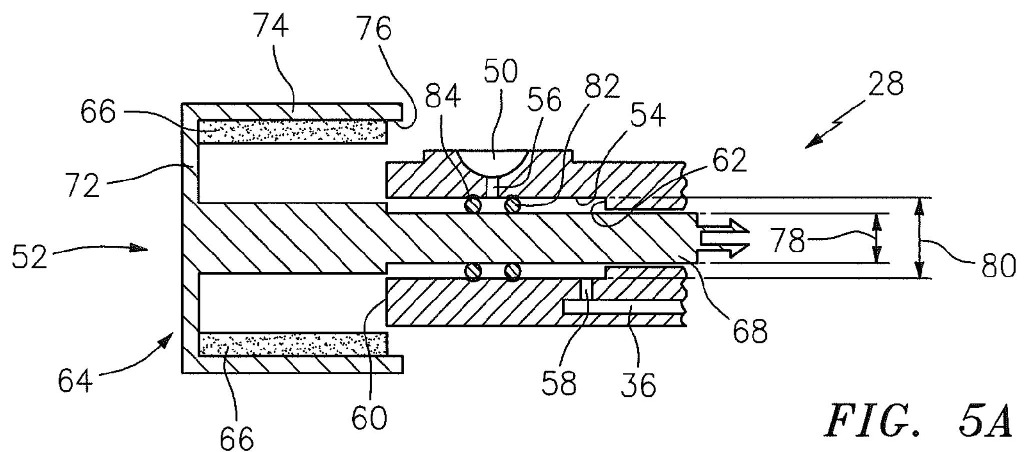
FIGS. 5A-5D are diagrammatic cross-sectional views of a collection port embodiment.
Figure 5B:
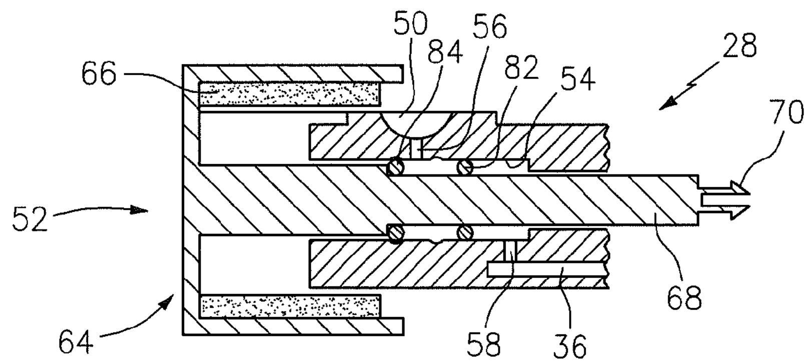
Figure 5C:
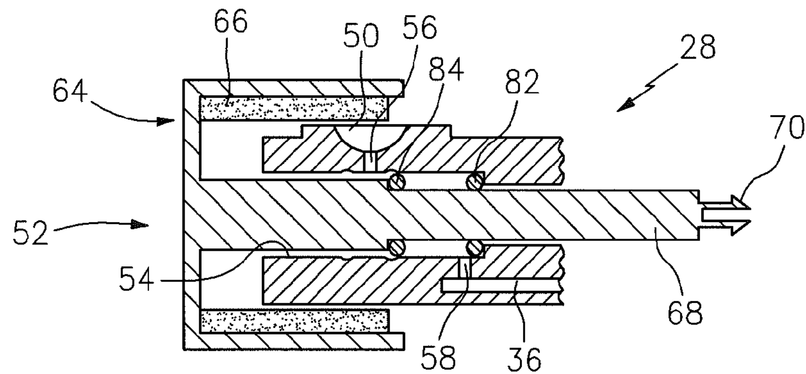
Figure 5D:
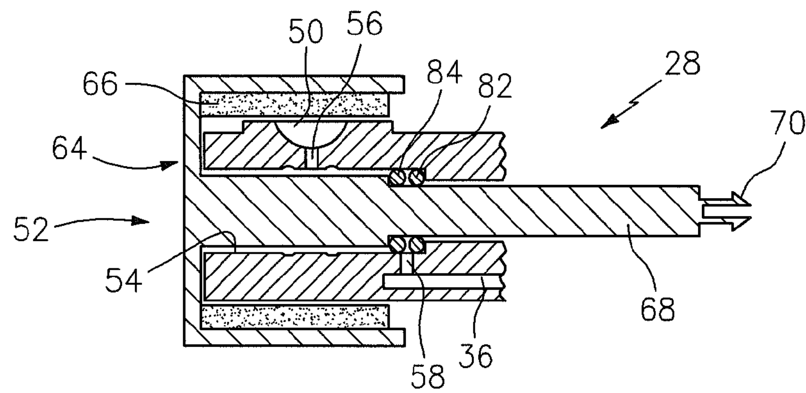

The cartridge body 30 includes one or more internal passages that extend from the collection port 28 to a transfer point 40, where sample can be transferred to the analysis chamber 32. In the embodiment shown in FIG. 4, the one or more internal passages include an initial channel 36 and a secondary channel 38. On one end of the initial channel 36, the channel is in fluid communication with the collection port 28. The term "fluid communication" is used herein to mean that a liquid passage exists between the structures, or out of a particular structure. On the other end of the initial channel 36, the channel is in fluid communication with the secondary channel 38. The initial channel 36 is sized such that capillary forces will act on liquids disposed within the initial channel 36. The intersection between the initial channel 36 and the secondary channel 38 is configured to stop fluid travel by capillary force and thereby prevent fluid sample from exiting the initial channel 36 and entering the secondary channel 38 absent an external motive force. The transfer point 40 between the secondary channel 38 and the analysis chamber 32 can assume a variety of different configurations; e.g., a portion of the secondary channel 38 may be contiguous with the analysis chamber 32, or an aperture may extend between the secondary channel 38 and the analysis chamber 32, or a metering channel sized to draw a volume of fluid sample out of the secondary channel 38 by capillary force, or an antechamber may be disposed between and in fluid communication with both the secondary channel 38 and an edge of analysis chamber 32, etc. The present invention is not limited to any particular transfer point 40 configuration.

For those cartridge 10 embodiments that require motive force to move fluid sample within one or more of the channels disposed in the cartridge body, the cartridge 10 may further include a fluid actuator port 42 configured to engage a sample motion system 22 incorporated with the analysis device 12. The fluid actuator port 42 is configured to permit a fluid motive force (e.g., positive air pressure and/or suction) to access the cartridge 10 to cause the fluid sample movement within the cartridge 10. The fluid actuator port 42 may be in fluid communication with the initial channel 36, for example, by a passage 44 extending between the fluid actuator port 42 and the initial channel 36. Prior to use, the fluid actuator port 42 may be covered by a rupturable seal material (e.g., adhesive tape, etc). The analysis device 12 includes structure that can access the fluid actuator port 42 (e.g., a probe operable to pierce the rupturable seal material) and thereby create fluid communication between the sample motion system 22 of the analysis device 12 and the initial and secondary channels 36, 38. The present cartridge 10 is not limited to this particular fluid actuator port 42 embodiment.

The analysis chamber 32 includes base chamber panel 46 and an upper chamber panel 48. At least one of the chamber panels 46, 48 has a transparent region. The interior surfaces of the panels 46, 48 are separated from one another by a distance referred to as the "chamber height". In preferred embodiments, the chamber includes a plurality of separators disposed between the two panels. The analysis chamber 32 is typically sized to hold about 0.2 to 1.0 μl of sample, but the chamber is not limited to any particular volume capacity, and the capacity can vary to suit the analysis application. The chamber is operable to quiescently hold a liquid sample. The term "quiescent" is used to describe that the sample is deposited within the chamber for analysis, and is not purposefully moved during the analysis. To the extent that motion is present within the blood sample residing within the analysis chamber 32, it will predominantly be due to Brownian motion of the blood sample's formed constituents, which motion is not disabling of the use of this invention. An example of an acceptable analysis chamber 32 is described in U.S. Patent Publication No. 2007/0243117, which is hereby incorporated by reference in its entirety.

Referring to FIGS. 5A-5D, in a first embodiment the collection port 28 includes a collection bowl 50 and a slide valve assembly 52. The slide valve assembly 52 is selectively movable between an open position (see FIG. 5A) wherein the collection bowl 50 can be accessed for sample deposition, and a closed position (see FIG. 5D) wherein the collection bowl 50 cannot be accessed. The collection bowl 50 is connected to the cartridge body 30, and is in fluid communication with a slide bore 54 through a bowl passage 56. The slide bore 54 is in fluid communication with the initial channel 36 through a bore passage 58. The slide bore 54 includes an entry end 60 and a bottom end 62.

In the embodiment shown in FIGS. 5A-5D, the slide valve assembly 52 includes a cap 64, a bowl seal 66, and a valve shaft 68. The cap 64 includes an interior cavity formed by an end panel 72 and one or more side panels 74 (referred to hereinafter as "a side panel" for ease of explanation). The side panel 74 extends outwardly from the end panel 72 and includes an interior surface 76. The valve shaft 68 is attached to the end panel 72 and is sized and positioned such that an annular region is formed between the valve shaft 68 and the interior surface 76 of the side panel 74. The bowl seal 66 is attached to the interior surface 76 of the side panel 74. As will be described below, the bowl seal 66 is positioned to extend over the collection bowl 50 when the slide valve assembly 52 is in the closed position. The bowl seal 66 may be formed of a seal material that seals the top of the collection bowl 50, or formed of an absorbent material that absorbs sample, or some combination thereof. The valve shaft 68 has a cross-sectional geometry that mates with the cross-sectional geometry of the slide bore 54; e.g., a male/female arrangement. The valve shaft 68 is described below as having an outer diameter 78 and the slide bore 54 is described as having an inner diameter 80. Although the valve shaft 68 and the slide bore 54 may have a circular cross-section, neither is limited to a circular cross-section, and the term "diameter" is used to describe relative dimensions of the two elements.

A seal arrangement is disposed between valve shaft 68 and the slide bore 54 that is operable to maintain liquid sample within a defined region, and move the sample within the slide bore 54. For example, the seal arrangement may include a first seal 82 and a second seal 84, one or both of which may be an o-ring, or a wiper type seal, etc. In the embodiment shown in FIGS. 5A-5D, the first seal 82 is located in a groove disposed in the valve shaft 68, and the second seal 84 is located in a groove disposed within slide bore 54. As indicated above, the seals 82, 84 are not limited to o-rings, and therefore the present invention is not limited to any particular structure for locating the seals (e.g., not limited to the grooves).

In the open position, the first seal 82 is disposed between the bore passage 58 and the bowl passage 56, in close proximity to the bowl passage 56. In the open position, the second seal 84 is located in close proximity to the bowl passage 56, between the bowl passage 56 and the slide bore entry end 60. In the open position, the first seal 82 prevents fluid communication between the bowl 50 and the bore passage 58, and the second seal 84 prevents fluid passage out of the slide bore 54. In the open position, the positions of the first and second seals 82, 84 relative to the bowl passage 56 and each other limit the amount of fluid sample that can enter the annular region disposed between the inner diameter 80 of the slide bore 54 and the outer diameter 78 of the valve shaft 68.

In the closed position, the first seal 82 is located on the side of the bore passage 58 that is opposite the side occupied by the first seal 82 in the open position; i.e., in the closed position, the first seal 82 is no longer disposed between the bowl passage 56 and the bore passage 58. In the closed position, the second seal 84 is positioned between the bowl passage 56 and the bore passage 58, in close proximity to the bore passage 58 and the first seal 82.

As the valve shaft 68 travels from the open position toward the closed position, initially the first seal 82 travels with the valve shaft 68 and the second seal 84 remains stationary relative to the slide bore 54. As a result, the annular region created between the first and second seals 82, 84, the bore inner diameter 80, and the valve shaft 68 outer diameter 78 increases in volume. The increase in volume creates a negative pressure that acts on sample residing within the bowl passage 56, drawing the sample into the annular region. Sample is drawn into the annular region until a shoulder (or other feature) disposed on the slide bore 54 engages the second seal 84, causing the second seal 84 to travel with the valve shaft 68 and pass over the bowl passage 56. For a portion of the valve shaft 68 travel between the open and closed positions, both the first and second seals 82, 84 travel with the shaft 68. Sample disposed within the annular region between the seals 82, 84 also travels with the valve shaft 68 further into the slide bore 54, toward the bottom end 62 of the slide bore 54. At a further point in the relative travel between the valve shaft 68 and the slide bore 54, the first seal 82 passes over the bore passage 58 and subsequently engages a shoulder (or other feature) extending out from the inner diameter of the slide bore 54, which feature prevents the first seal 82 from traveling further with the valve shaft 68. At this point, the first seal 82 is stationary relative to the slide bore 54 and the second seal 84 continues to travel with the valve shaft 68. As a result, the annular region created between the seals 82, 84 decreases in volume, causing the sample within the annular region to exit the annular region through the bore passage 58, and into the initial channel 36. When the slide assembly 52 reaches the closed position, the annular region volume is decreased by an amount that is at least equal to the volume of fluid sample intended to enter the analysis chamber 32 for subsequent processing and analysis.

In some embodiments, the slide valve assembly 52 may include a latch mechanism 70 that holds the slide valve assembly 52 in one or both of the open and closed positions. In a preferred embodiment, the latch mechanism 70 is operable to lock the slide valve assembly 52 in the closed position once the sample has been loaded to prevent contamination of the sample or spillage, thereby increasing the safety of the cartridge 10.

Figure 6A:
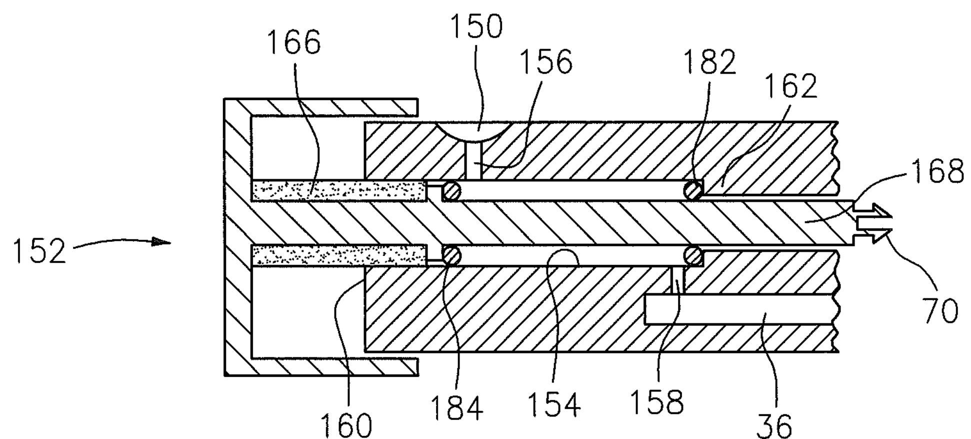
FIGS. 6A and 6B are diagrammatic cross-sectional views of a collection port embodiment.
Figure 6B:
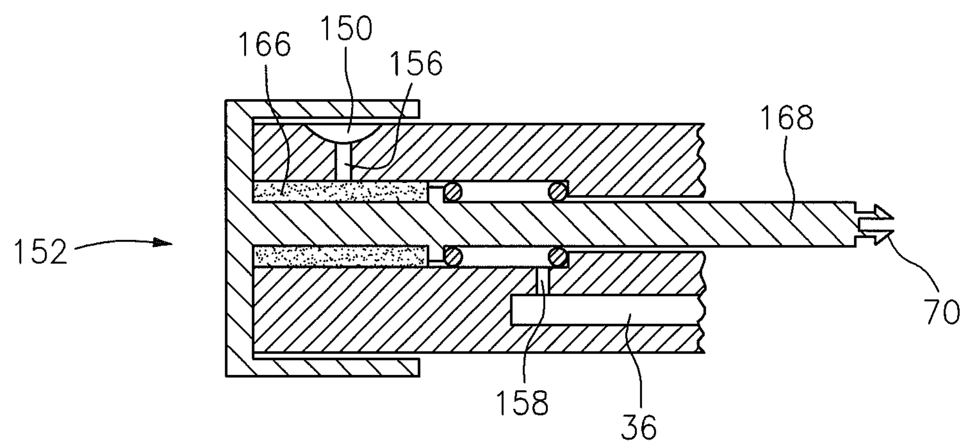

In another embodiment shown in FIGS. 6A and 6B, the collection port 28 includes a collection bowl 150 and a slide valve assembly 152 similar to that shown in FIGS. 5A-5D. In the closed position, the bowl seal 166, which is attached to the valve shaft 168, is disposed within the slide bore 154 and aligned with the bowl passage 156. In this position, the bowl seal 166 prevents fluid passage between the slide bore 154 and the bowl passage 156. Also in this embodiment, the first seal 182 is attached to the slide bore 154 and the second seal 184 is attached to the valve shaft 168. The first seal 182 remains stationary relative to the slide bore 154 for the entire valve shaft travel between the opened and closed positions, and the second seal 184 moves with the valve shaft 168 for the entire travel between the opened and closed positions. As indicated above, the first and second seals 182, 184 (e.g., o-rings, wiper seals, etc.) are not limited to any particular type of seal.

In both the open and closed positions, the first seal 182 is disposed between the bore passage 158 and the slide bore bottom end 162, in close proximity to the bore passage 158. In the open position, the second seal 184 is located between the bowl passage 156 and the slide bore entry end 160, in close proximity to the bowl passage 156. In the open position, the first seal 182 prevents fluid passage out the bottom end 162 of the slide bore 154 and the second seal 184 prevents fluid passage out of the entry end 160 of the slide bore 154. In the open position, sample is allowed to enter the annular region between the inner diameter 180 of the slide bore 154 and the outer diameter 178 of the valve shaft 168. In the closed position, the second seal 184 is positioned between the bowl passage 156 and the bore passage 158, in close proximity to the bore passage 158 and the first seal 182.

As the valve shaft 168 travels from the open position toward the closed position, the second seal 184 travels with the valve shaft 168 causing the annular region between the valve shaft 168 and the slide bore 154 to decrease in volume. As a result, sample within the annular region is forced to exit the annular region through the bore passage 158, and into the initial channel 36. When the slide valve assembly 152 reaches the closed position, the annular region volume is decreased by an amount that is at least equal to the volume of fluid sample intended to enter the analysis chamber 32 for subsequent processing and analysis. This embodiment may also include a latch mechanism 70 such as that described above operable to hold the slide valve assembly 152 in one or both of the open and closed positions.

Figure 7A:
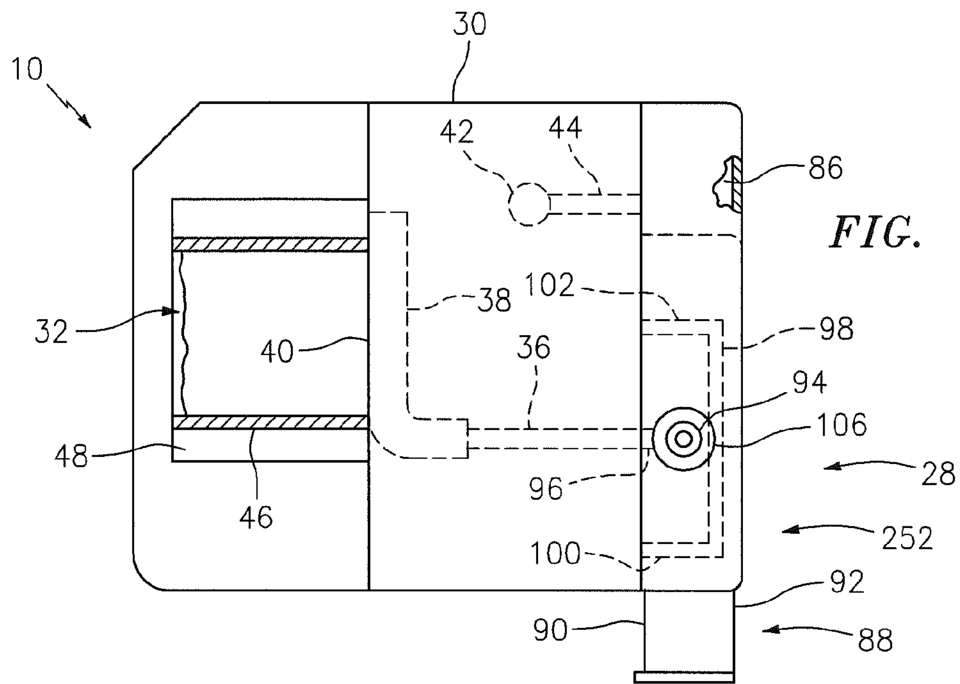
FIGS. 7A-7C are diagrammatic views of a collection port embodiment.
Figure 7B:
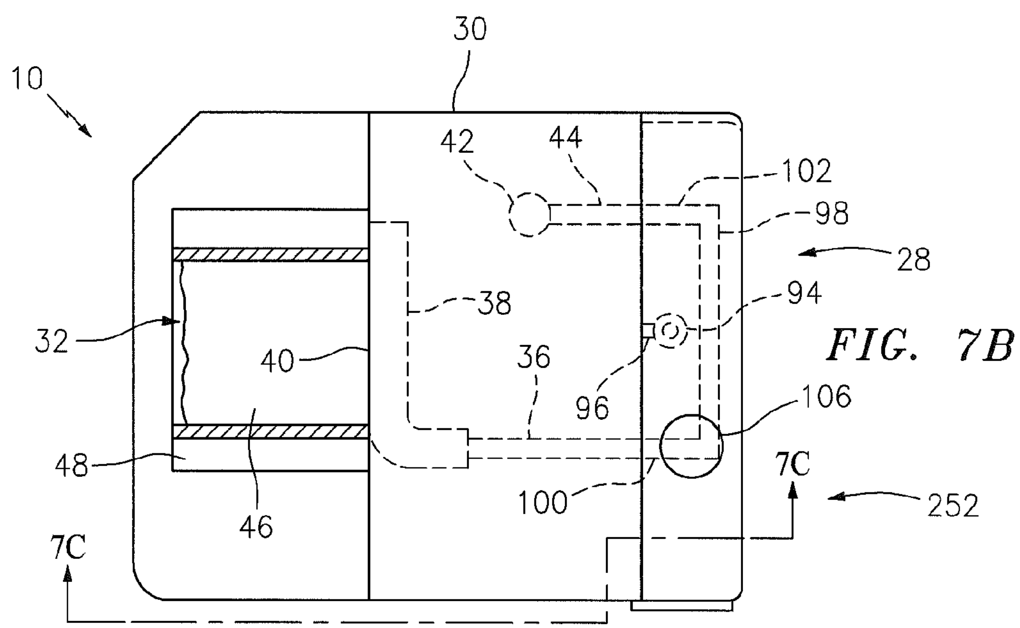
Figure 7C:
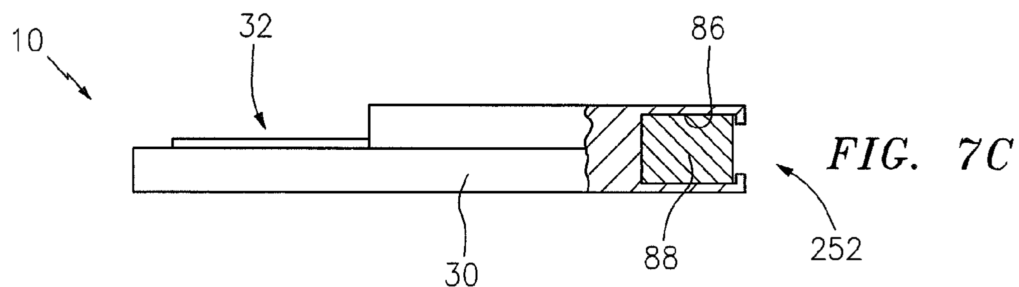

In another embodiment shown in FIGS. 7A-7C, the cartridge 10 includes a collection port 28 having a slide valve assembly 252 received within a channel 86 disposed along an edge of the cartridge 10. The slide valve assembly 252 includes a slide body 88 having a first side 90, a second side 92, a collection bowl 94, a bowl passage 96, and an internal passage 98 having a first end 100 and a second end 102. The first and second sides 90, 92 extend lengthwise along the slide body 88, each on an opposite from the other. The bowl passage 96 extends between the first side 90 and the collection bowl 94, providing fluid communication there between. The first and second ends 100, 102 of the internal passage 98 are each disposed in the first side 90, spaced apart from one another. Each end 100, 102 of the internal passage 98 is disposed on an opposite side of the bowl passage 96. The widthwise cross-sectional geometry of the slide body 88 mates with the channel 86 and permits the slide body 88 to travel within the channel 86. In some embodiments, the slide body 88 and the channel 86 form a press fit that is strong enough to hold the relative positions in the absence of external force, but weak enough to allow the slide body 88 to be moved within the channel 86 by an operator's hand force. In some embodiments, one of the slide body 88 or channel 86 is formed of a material that is more pliable than the material of the other and capable of making a seal between the two. The channel 86 includes features 104 that hold the slide body 88 within the channel 86, and also a port 106 sized to permit fluid sample passage through to the collection bowl 94.

In the open position (see FIG. 7A), a portion of the slide body 88 extends out from the channel 86, and the port 106 is aligned with the collection bowl 94 to allow passage of sample through the port 106, into the collection bowl 94, into the bowl passage 96 and finally into the initial channel 36 of the cartridge 10. Capillary force acting on the sample (and/or gravity) draws the sample from the collection bowl 94 and into the initial channel 36. The first and second ends 100, 102 of the internal passage 98 are aligned with a wall of channel 86 and therefore not open to any fluid flow in the open position.

In the closed position (see FIG. 7B): 1) the slide body 88 is received further within the channel 86; 2) the port 106 is not aligned with the collection bowl 94; 3) the collection bowl 94 is closed within the channel 86; 4) the bowl passage 96 is not aligned with the initial channel 36 and is, instead, closed by a wall of the channel 86; and 5) the first end 100 of the internal passage 98 is aligned with the initial channel 36, and the second end 102 of the internal passage 98 is aligned with a passage 44 extending to a fluid actuator port 42. The internal passage 98, therefore, makes a fluid communication connection between the fluid actuator port 42 and the initial channel 36. Motive force produced by the sample motion system 22 (e.g., pressurized air from a bidirectional fluid actuator—see FIG. 1) can be passed from the fluid actuator port 42 through to the initial channel 36, where it can be used to move the sample into the secondary channel 38, for sample mixing, to force the sample into the analysis chamber 32, etc.

In the operation of the cartridge 10, a sample of biologic fluid is deposited in the collection bowl of the cartridge 10. In the collection bowl embodiments shown in FIGS. 5A-5D and 6A-6B, the sample is moved into the initial channel 36 by the slide valve assembly 52, 152 being moved from the open position to the closed position. In the collection bowl embodiment shown in FIGS. 7A-7C, the sample is moved into the initial channel 36 by capillary action while the slide valve assembly 252 is in the open position.

In those cartridge 10 embodiments that are configured to utilize an external motive force to move the sample within the cartridge 10, that force is subsequently used to move the sample from the initial channel 36, into the secondary channel 38, and then to the analysis chamber 32. Once in the analysis chamber 32, the quiescently residing sample is imaged for subsequent analysis.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A biological fluid sample analysis cartridge, comprising:

a collection port;

a seal arrangement; and a body having one or more internal channels in selective fluid communication with the collection port;

wherein the collection port includes a collection bowl, and a slide valve assembly operable to be selectively positioned in an open position and a closed position;

wherein in the open position, the collection bowl is accessible for sample deposition, and in the closed position the collection bowl is inaccessible for sample deposition;

wherein the slide valve assembly includes a valve shaft that is received within a slide bore disposed in the body of the cartridge, and the slide valve assembly is operable to force sample into the one or more internal channels when the slide valve assembly is moved from the open position to the closed position;

wherein the seal arrangement is disposed between the valve shaft and the slide bore and includes a first seal located in a first groove disposed in the valve shaft and a second seal located in a second groove disposed within the slide bore.

2. The cartridge of claim 1, wherein the seal arrangement is operable to move sample within the slide bore.

3. The cartridge of claim 2, further comprising a first passage extending between the collection bowl and the slide bore, and a second passage extending between the internal channel and the slide bore.

4. The cartridge of claim 3, wherein in the open position, the seal arrangement prevents fluid communication between the collection bowl and the second passage, and prevents fluid passage out of the slide bore.

5. The cartridge of claim 4, wherein the seal arrangement is operable to draw sample out of the first passage and into the slide bore for a portion of relative travel between the valve shaft and the slide bore.

6. The cartridge of claim 5, wherein the seal arrangement is operable to propel sample out of the slide bore and into the second passage for a portion of relative travel between the valve shaft and the slide bore.

7. The cartridge of claim 1, further comprising an analysis chamber, wherein the internal channels are in selective fluid communication with the analysis chamber.

8. The cartridge of claim 1, wherein the slide valve assembly includes a cap having an interior cavity wherein an annular region is disposed between the valve shaft and an interior surface of the cap.

9. The cartridge of claim 3, further comprising a bowl seal disposed to extend over the collection bowl when the slide valve assembly is in the closed position.

10. The cartridge of claim 1, wherein in the closed position, the collection port is inaccessible.

11. The cartridge of claim 1, wherein in the open position the first seal is disposed between a bore passage and a bowl passage on a first side of the bore passage, and wherein in the open position the second seal is disposed between the bowl passage and an entry end of the slide bore.

12. The cartridge of claim 11, wherein in the closed position the first seal is located on a second side of the bore passage that is opposite to the first side of the bore passage, and wherein in the closed position the second seal is positioned between the bowl passage and the bore passage.

* * * * *